(12) United States Patent
Garrison (10) Patent No.: US 9,308,012 B2
(45) Date of Patent: *Apr. 12, 2016

(54) ARTICULATING SURGICAL APPARATUS

(71) Applicant: COVIDIEN LP, Mansfield, MA (US)

(72) Inventor: David M. Garrison, Longmont, CO (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/612,517

(22) Filed: Feb. 3, 2015

(65) Prior Publication Data

US 2015/0148802 A1 May 28, 2015

Related U.S. Application Data (63) Continuation of application No. 13/412,879, filed on Mar. 6, 2012, now Pat. No. 8,961,514.

(51) Int. Cl.
*A61B 18/18* (2006.01)
*A61B 17/29* (2006.01)
*A61B 17/295* (2006.01)
*A61B 17/00* (2006.01)
(Continued)

(52) U.S. Cl.
CPC .............. *A61B 17/29* (2013.01); *A61B 17/295* (2013.01); *A61B 18/1445* (2013.01); *A61B 2017/003* (2013.01); *A61B 2017/2936* (2013.01); *A61B 2018/0063* (2013.01); *A61B 2018/1455* (2013.01)

(58) Field of Classification Search
CPC .. A61B 17/29; A61B 17/295; A61B 18/1445; A61B 2017/003; A61B 2017/2936; A61B 2018/0063; A61B 2018/1455
See application file for complete search history.

(56) References Cited

U.S. PATENT DOCUMENTS

| 3,190,286 | A | 6/1965 | Stokes |
| 3,788,303 | A | 1/1974 | Hall |
| D249,549 | S | 9/1978 | Pike |

(Continued)

FOREIGN PATENT DOCUMENTS

| CN | 201299462 | | 9/2009 |
| DE | 2415263 | A1 | 10/1975 |

(Continued)

OTHER PUBLICATIONS

Int'l Search Report EP 07 015601.3 dated Jan. 4, 2008.

(Continued)

*Primary Examiner* — George Manuel (57) ABSTRACT

An endoscopic forceps is provided. The endoscopic forceps includes a housing having a shaft that extends therefrom that defines a longitudinal axis therethrough. The shaft has a first tube with a bent portion having a contour. A second tube is disposed within the first tube. An end effector assembly operatively connected to a distal end of the first tube has a pair of first and second jaw members. The first and second jaw members including respective cam slots defined therein with a cam pin movable therein. The shaft is translatable along the longitudinal axis to straighten the bent portion of the first tube to move the bent portion of the first tube from an articulated configuration to a non-articulated configuration. The second tube is translatable along the longitudinal axis to move the first and second jaw members from the open configuration to the clamping configuration.

19 Claims, 5 Drawing Sheets

(51) Int. Cl.
*A61B 18/14* (2006.01)
*A61B 18/00* (2006.01)

(56) References Cited

U.S. PATENT DOCUMENTS

| | | | |
|---|---|---|---|
| D263,020 S | 2/1982 | Rau, III | |
| D295,893 S | 5/1988 | Sharkany et al. | |
| D295,894 S | 5/1988 | Sharkany et al. | |
| D298,353 S | 11/1988 | Manno | |
| D299,413 S | 1/1989 | DeCarolis | |
| 5,195,968 A | 3/1993 | Lundquist et al. | |
| D343,453 S | 1/1994 | Noda | |
| D348,930 S | 7/1994 | Olson | |
| D349,341 S | 8/1994 | Lichtman et al. | |
| D354,564 S | 1/1995 | Medema | |
| D358,887 S | 5/1995 | Feinberg | |
| 5,411,519 A | 5/1995 | Tovey et al. | |
| 5,487,757 A | 1/1996 | Truckai et al. | |
| D384,413 S | 9/1997 | Zlock et al. | |
| H1745 H | 8/1998 | Paraschac | |
| D402,028 S | 12/1998 | Grimm et al. | |
| D408,018 S | 4/1999 | McNaughton | |
| D416,089 S | 11/1999 | Barton et al. | |
| D424,694 S | 5/2000 | Tetzlaff et al. | |
| D425,201 S | 5/2000 | Tetzlaff et al. | |
| 6,077,287 A | 6/2000 | Taylor et al. | |
| H1904 H | 10/2000 | Yates et al. | |
| D449,886 S | 10/2001 | Tetzlaff et al. | |
| D453,923 S | 2/2002 | Olson | |
| D454,951 S | 3/2002 | Bon | |
| D457,958 S | 5/2002 | Dycus et al. | |
| D457,959 S | 5/2002 | Tetzlaff et al. | |
| H2037 H | 7/2002 | Yates et al. | |
| D465,281 S | 11/2002 | Lang | |
| D466,209 S | 11/2002 | Bon | |
| 6,656,195 B2 * | 12/2003 | Peters et al. | 606/159 |
| D493,888 S | 8/2004 | Reschke | |
| D496,997 S | 10/2004 | Dycus et al. | |
| D499,181 S | 11/2004 | Dycus et al. | |
| D502,994 S | 3/2005 | Blake, III | |
| 6,911,029 B2 | 6/2005 | Platt | |
| D509,297 S | 9/2005 | Wells | |
| D525,361 S | 7/2006 | Hushka | |
| D531,311 S | 10/2006 | Guerra et al. | |
| D533,274 S | 12/2006 | Visconti et al. | |
| D533,942 S | 12/2006 | Kerr et al. | |
| D535,027 S | 1/2007 | James et al. | |
| D538,932 S | 3/2007 | Malik | |
| D541,418 S | 4/2007 | Schechter et al. | |
| D541,611 S | 5/2007 | Aglassinger | |
| D541,938 S | 5/2007 | Kerr et al. | |
| D545,432 S | 6/2007 | Watanabe | |
| D547,154 S | 7/2007 | Lee | |
| D564,662 S | 3/2008 | Moses et al. | |
| D567,943 S | 4/2008 | Moses et al. | |
| D575,395 S | 8/2008 | Hushka | |
| D575,401 S | 8/2008 | Hixson et al. | |
| D582,038 S | 12/2008 | Swoyer et al. | |
| 7,686,826 B2 * | 3/2010 | Lee et al. | 606/205 |
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| D618,798 S | 6/2010 | Olson et al. | |
| D621,503 S | 8/2010 | Otten et al. | |
| D627,462 S | 11/2010 | Kingsley | |
| D628,289 S | 11/2010 | Romero | |
| D628,290 S | 11/2010 | Romero | |
| D630,324 S | 1/2011 | Reschke | |
| D649,249 S | 11/2011 | Guerra | |
| D649,643 S | 11/2011 | Allen, Iv et al. | |
| 8,409,246 B2 | 4/2013 | Kerr et al. | |
| 8,469,716 B2 | 6/2013 | Fedotov et al. | |
| 8,568,408 B2 | 10/2013 | Townsend et al. | |
| 8,591,510 B2 | 11/2013 | Allen, IV et al. | |
| 8,628,557 B2 | 1/2014 | Collings et al. | |
| 8,679,098 B2 | 3/2014 | Hart | |
| 8,685,009 B2 | 4/2014 | Chernov et al. | |
| 8,685,021 B2 | 4/2014 | Chernov et al. | |
| 8,685,056 B2 | 4/2014 | Evans et al. | |
| 8,702,737 B2 | 4/2014 | Chojin et al. | |
| 8,702,749 B2 | 4/2014 | Twomey | |
| 8,745,840 B2 | 6/2014 | Hempstead et al. | |
| 8,747,434 B2 | 6/2014 | Larson et al. | |
| 8,756,785 B2 | 6/2014 | Allen, IV et al. | |
| 8,784,418 B2 | 7/2014 | Romero | |
| 8,840,639 B2 | 9/2014 | Gerhardt, Jr. et al. | |
| 8,845,636 B2 | 9/2014 | Allen, IV et al. | |
| 8,852,185 B2 | 10/2014 | Twomey | |
| 8,852,228 B2 | 10/2014 | Nau, Jr. | |
| 8,864,753 B2 | 10/2014 | Nau, Jr. et al. | |
| 8,864,795 B2 | 10/2014 | Kerr et al. | |
| 8,887,373 B2 | 11/2014 | Brandt et al. | |
| 8,898,888 B2 | 12/2014 | Brandt et al. | |
| 8,900,232 B2 | 12/2014 | Ourada | |
| 8,920,421 B2 | 12/2014 | Rupp | |
| 8,932,293 B2 | 1/2015 | Chernov et al. | |
| 8,936,614 B2 | 1/2015 | Allen, IV | |
| 8,939,972 B2 | 1/2015 | Twomey | |
| 8,945,175 B2 | 2/2015 | Twomey | |
| 8,961,513 B2 | 2/2015 | Allen, IV et al. | |
| 8,961,514 B2 | 2/2015 | Garrison | |
| 8,961,515 B2 | 2/2015 | Twomey et al. | |
| 8,968,283 B2 | 3/2015 | Kharin | |
| 8,968,305 B2 | 3/2015 | Dumbauld et al. | |
| 8,968,306 B2 | 3/2015 | Unger | |
| 8,968,307 B2 | 3/2015 | Evans et al. | |
| 8,968,308 B2 | 3/2015 | Horner et al. | |
| 8,968,309 B2 | 3/2015 | Roy et al. | |
| 8,968,310 B2 | 3/2015 | Twomey et al. | |
| 8,968,316 B2 | 3/2015 | Roy et al. | |
| 8,968,317 B2 | 3/2015 | Evans et al. | |
| 8,968,360 B2 | 3/2015 | Garrison et al. | |
| 9,011,435 B2 | 4/2015 | Brandt et al. | |
| 2010/0280526 A1 | 11/2010 | Weisel et al. | |
| 2011/0118757 A1 | 5/2011 | Pierce | |
| 2012/0123404 A1 * | 5/2012 | Craig | 606/33 |
| 2012/0123410 A1 * | 5/2012 | Craig | 606/41 |
| 2012/0130367 A1 * | 5/2012 | Garrison | 606/41 |
| 2012/0172868 A1 * | 7/2012 | Twomey et al. | 606/41 |
| 2012/0184990 A1 * | 7/2012 | Twomey | 606/206 |
| 2012/0209263 A1 * | 8/2012 | Sharp et al. | 606/45 |
| 2012/0239034 A1 * | 9/2012 | Horner et al. | 606/51 |
| 2012/0259331 A1 * | 10/2012 | Garrison | 606/51 |
| 2012/0265241 A1 * | 10/2012 | Hart et al. | 606/205 |
| 2012/0296205 A1 * | 11/2012 | Chernov et al. | 600/431 |
| 2012/0296238 A1 * | 11/2012 | Chernov et al. | 601/2 |
| 2012/0296239 A1 * | 11/2012 | Chernov et al. | 601/2 |
| 2012/0296317 A1 * | 11/2012 | Chernov et al. | 606/2 |
| 2012/0296323 A1 * | 11/2012 | Chernov | A61B 18/20 606/13 |
| 2012/0296324 A1 * | 11/2012 | Chernov | A61B 18/20 606/16 |
| 2012/0303025 A1 * | 11/2012 | Garrison | A61B 17/29 606/51 |
| 2012/0323238 A1 * | 12/2012 | Tyrrell | A61B 18/1445 606/52 |
| 2012/0330308 A1 * | 12/2012 | Joseph | A61B 18/1442 606/45 |
| 2012/0330309 A1 * | 12/2012 | Joseph | A61B 18/1442 606/45 |
| 2013/0018364 A1 * | 1/2013 | Chernov | A61B 17/122 606/14 |
| 2013/0018372 A1 * | 1/2013 | Sims | A61B 17/285 606/45 |
| 2013/0022495 A1 * | 1/2013 | Allen, IV | A61L 2/08 422/24 |
| 2013/0046295 A1 * | 2/2013 | Kerr | A61B 18/1445 606/41 |
| 2013/0060250 A1 * | 3/2013 | Twomey | A61B 18/1447 606/52 |
| 2013/0066318 A1 * | 3/2013 | Kerr | A61B 17/29 606/52 |
| 2013/0071282 A1 * | 3/2013 | Fry | B22F 3/225 |

(56) References Cited

U.S. PATENT DOCUMENTS

| | | | | |
|---|---|---|---|---|
| 2013/0072927 | A1* | 3/2013 | Allen et al. | 419/8<br>606/41 |
| 2013/0079760 | A1* | 3/2013 | Twomey et al. | 606/13 |
| 2013/0079774 | A1* | 3/2013 | Whitney et al. | 606/52 |
| 2013/0085491 | A1* | 4/2013 | Twomey et al. | 606/41 |
| 2013/0085496 | A1* | 4/2013 | Unger et al. | 606/45 |
| 2013/0103030 | A1* | 4/2013 | Garrison | 606/42 |
| 2013/0103031 | A1* | 4/2013 | Garrison | 606/42 |
| 2013/0138101 | A1* | 5/2013 | Kerr | 606/45 |
| 2013/0138129 | A1* | 5/2013 | Garrison et al. | 606/170 |
| 2013/0144284 | A1* | 6/2013 | Behnke et al. | 606/33 |
| 2013/0178852 | A1* | 7/2013 | Allen et al. | 606/42 |
| 2013/0185922 | A1* | 7/2013 | Twomey et al. | 29/527.1 |
| 2013/0197503 | A1* | 8/2013 | Orszulak | 606/33 |

FOREIGN PATENT DOCUMENTS

| | | |
|---|---|---|
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 19946527 C1 | 7/2001 |
| DE | 10045375 C2 | 10/2002 |
| DE | 20 2007 009317 U1 | 8/2007 |
| DE | 202007009165 U1 | 8/2007 |
| DE | 202007016233 U1 | 1/2008 |
| DE | 19738457 B4 | 1/2009 |
| DE | 102004026179 B4 | 1/2009 |
| DE | 102008018406 B3 | 7/2009 |
| EP | 1 159 926 A2 | 12/2001 |
| JP | 61-501068 | 9/1984 |
| JP | 10-24051 A | 1/1989 |
| JP | 11-47150 A | 6/1989 |
| JP | 6-502328 | 3/1992 |
| JP | 5-5106 | 1/1993 |
| JP | 05-40112 | 2/1993 |
| JP | 0006030945 A | 2/1994 |
| JP | 6-121797 A | 5/1994 |
| JP | 6-285078 A | 10/1994 |
| JP | 6-511401 | 12/1994 |
| JP | 06343644 A | 12/1994 |
| JP | 07265328 A | 10/1995 |
| JP | 8-56955 | 5/1996 |
| JP | 08252263 A | 10/1996 |
| JP | 8-289895 A | 11/1996 |
| JP | 8-317934 A | 12/1996 |
| JP | 8-317936 A | 12/1996 |
| JP | 9-10223 C | 1/1997 |
| JP | 9-122138 A | 5/1997 |
| JP | 10-155798 A | 6/1998 |
| JP | 11-070124 A | 3/1999 |
| JP | 11-169381 A | 6/1999 |
| JP | 11-192238 A | 7/1999 |
| JP | 11244298 A | 9/1999 |
| JP | 2000-102545 A | 4/2000 |
| JP | 2000342599 A | 12/2000 |
| JP | 2000350732 A | 12/2000 |
| JP | 2001-8944 | 1/2001 |
| JP | 2001-29356 | 2/2001 |
| JP | 2001128990 A | 5/2001 |
| JP | 2001-190564 A | 7/2001 |
| JP | 20013400 | 11/2001 |
| JP | 2002-528166 A | 9/2002 |
| JP | 2003245285 A | 9/2003 |
| JP | 2004-517668 A | 6/2004 |
| JP | 2004-528869 A | 9/2004 |
| JP | 2011125195 A | 6/2011 |
| SU | 401367 A1 | 10/1973 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 2005/110264 A2 | 11/2005 |

OTHER PUBLICATIONS

Int'l Search Report EP 07 016911 dated May 28, 2010.
Int'l Search Report EP 07 016911.5 extended dated Mar. 2, 2011.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 011750.6 dated Feb. 1, 2011.
Int'l Search Report EP 10 157500.9 dated Jul. 30, 2010.
Int'l Search Report EP 10 159205.3 dated Jul. 7, 2010.
Int'l Search Report EP 10 160870.1 dated Aug. 9, 2010.
Int'l Search Report EP 10 161596.1 dated Jul. 28, 2010.
Int'l Search Report EP 10 167655.9 dated Aug. 31, 2011.
Int'l Search Report EP 10 168705.1 dated Oct. 4, 2010.
Int'l Search Report EP 10 169647.4 dated Oct. 29, 2010.
Int'l Search Report EP 10 172005.0 dated Sep. 30, 2010.
Int'l Search Report EP 10 175956.1 dated Nov. 12, 2010.
Int'l Search Report EP 10 181034.9 dated Jan. 26, 2011.
Int'l Search Report EP 10 181575.1 dated Apr. 5, 2011.
Int'l Search Report EP 10 181969.6 dated Feb. 4, 2011.
Int'l Search Report EP 10 182019 dated Aug. 4, 2011.
Int'l Search Report EP 10 182022.3 dated Mar. 11, 2011.
Int'l Search Report EP 10 185386.9 dated Jan. 10, 2011.
Int'l Search Report EP 10 185405.7 dated Jan. 5, 2011.
U.S. Appl. No. 08/926,869, filed Sep. 10, 1997, James G. Chandler.
U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, filed Jun. 9, 2000, Thomas P. Ryan.
U.S. Appl. No. 12/336,970, filed Dec. 17, 2008, Paul R. Sremcich.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967, British Medical Journal Feb. 6, 1976, vol. 1, nr. 5431 p. 361, ISSN: 0007-1447.

(56) References Cited

OTHER PUBLICATIONS

Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte,NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.

Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 10 186527.7 dated Jun. 17, 2011.
Int'l Search Report EP 10 189206.5 dated Mar. 17, 2011.
Int'l Search Report EP 10 191320.0 dated Feb. 15, 2011.
Int'l Search Report EP 11 151509.4 dated Jun. 6, 2011.
Int'l Search Report EP 11 152220.7 dated May 19, 2011.
Int'l Search Report EP 11 152360.1 dated Jun. 6, 2011.
Int'l Search Report EP 11 159771.2 dated May 28, 2010.
Int'l Search Report EP 11 161117.4 dated Jun. 30, 2011.
Int'l Search Report EP 11 161118.2 dated Oct. 12, 2011.
Int'l Search Report EP 11 164274.0 dated Aug. 3, 2011.
Int'l Search Report EP 11 164275.7 dated Aug. 25, 2011.
Int'l Search Report EP 11 167437.0 dated Aug. 8, 2011.
Int'l Search Report EP 11 168458.5 dated Jul. 29, 2011.
Int'l Search Report EP 11 173008.1 dated Nov. 4, 2011.
Int'l Search Report EP 11 179514 dated Nov. 4, 2011.
Int'l Search Report EP 11 180182.5 dated Nov. 15, 2011.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.

(56) References Cited

OTHER PUBLICATIONS

Int'l Search Report PCT/US03/18674 dated Sep. 18, 2003.
Int'l Search Report PCT/US03/18676 dated Sep. 19, 2003.
Int'l Search Report PCT/US03/28534 dated Dec. 19, 2003.
Int'l Search Report PCT/US03/28539 dated Jan. 6, 2004.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04709033.7 dated Dec. 8, 2010.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 004429.2 dated Nov. 2, 2010.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.

* cited by examiner

ARTICULATING SURGICAL APPARATUS

CROSS-REFERENCE TO RELATED APPLICATIONS

This application is a continuation application of U.S. patent application Ser. No. 13/412,879, filed on Mar. 6, 2012, the entire contents of which are incorporated herein by reference.

BACKGROUND

1. Technical Field

The present disclosure relates to an articulating surgical apparatus. More particularly, the present disclosure relates to an articulating surgical apparatus including a shaft in coaxial relation with a first tube having a pre-formed bent configuration.

2. Description of Related Art

Surgical instruments that are configured to articulate or bend are well known in the medical arts. Surgical instruments of this nature are utilized in many surgical procedures. For example, laparoscopic, endoscopic, or other minimally invasive surgical procedures are just a few of the many surgical procedures where articulating surgical instruments may find use. When utilized in such procedures, the surgical instruments may include a housing, a handle assembly, an articulating shaft, a device for articulating the shaft, and an end effector including a pair of jaw members.

As can be appreciated, the relatively small operable working space that is created within a cavity of a patient during an endoscopic surgical procedure often makes it difficult for the surgeon to position the jaw members adjacent or close to target tissue. An articulating shaft allows a surgeon to position the jaw members adjacent target tissue.

Various articulating devices or mechanisms may be utilized to articulate the shaft. For example, some surgical instruments utilize one or more articulating cables or tendons that couple to one or more articulation links on the shaft. Typically, the cables or tendons provide a mechanical interface from the one or more articulation links to an actuation device, e.g., rotatable dials, disposed on the housing and/or handle assembly of the surgical instrument such that actuation of the actuation device moves or articulates the shaft about the articulation links. In particular, the cables or tendons are "pulled" or otherwise manipulated via one or more mechanisms in the handle assembly or the housing to articulate the shaft about the articulating links. As can be appreciated, having to add articulating links and/or tendons to the surgical instrument may further increase manufacturing costs of the surgical instrument and/or increase production time of the electrosurgical endoscopic instrument.

SUMMARY

In view of the foregoing, there may be a need for an articulating surgical apparatus including a shaft in coaxial relation with a first tube having a pre-formed bent configuration.

An aspect of the present disclosure provides an endoscopic forceps. The endoscopic forceps includes a housing having a shaft that extends therefrom that defines a longitudinal axis therethrough. The shaft has a first tube coaxially disposed therein having a bent portion at a distal end thereof having a contour. The shaft has a second tube disposed therein having a bent portion that follows the contour of the bent portion of the first tube. An end effector assembly is operatively connected to a distal end of the first tube and has a pair of first and second jaw members. The first and second jaw members are moveable from an open position for positioning tissue to a clamping position for clamping tissue therebetween. The first and second jaw members include respective cam slots defined therein with a cam pin movable therein. The cam pin operably coupling the second tube to the first and second jaw members. The shaft is translatable along the longitudinal axis to straighten the bent portion of the first tube to move the bent portion of the first tube from an articulated configuration to a non-articulated configuration and the second tube is translatable along the longitudinal axis to move the first and second jaw members from the open configuration to the clamping configuration.

The second tube may be configured to house a cutter shaft therein. The cutter shaft may include a knife assembly having a knife blade configured to reciprocate through knife channels operably disposed on the first and second jaw members upon activation of a trigger assembly associated with the endoscopic forceps. An elongated slot may be defined in at least a portion of the knife assembly and is configured to house a pivot pin and the cam pin therein such that the first and second jaw members are movable independent of the knife assembly.

The endoscopic forceps may be configured to electrosurgically treat tissue and is adapted to connect to a source of electrosurgical energy via a cable.

The second tube may be configured to house a pair of leads of the cable to electrically couple respective seal plates of the first and second jaw members to the source of electrosurgical energy.

A degree of curvature of the bent portion of first tube and a degree of curvature of the bent portion of the second tube may range from about 10 degrees to about 120 degrees.

In certain instance, the endoscopic forceps may include a handle assembly having a movable handle movable relative to a fixed handle. In this instance, the movable handle may be operatively connected to a drive assembly that together mechanically cooperate to impart movement of the second tube.

An aspect of the present disclosure provides an endoscopic forceps. The endoscopic forceps includes a housing having a shaft that extends therefrom that defines a longitudinal axis therethrough. The shaft is translatable along the longitudinal axis and has a plurality of tubes including a first tube coaxially disposed therein and a second tube coaxially disposed within the first tube. The first and second tubes each have a respective bent portion at a distal end thereof. The shaft and second tube are each translatable along the longitudinal axis with respect to the first tube. An end effector assembly is operatively connected to a distal end of the first tube and has a pair of first and second jaw members moveable from an open position for positioning tissue to a clamping position for clamping tissue therebetween. The first and second jaw members include respective cam slots defined therein with a cam pin movable therein, the cam pin operably coupling the second tube to the first and second jaw members. The shaft is translatable along the longitudinal axis to straighten the bent portion of the first and second tubes to move the bent portion of the first and second tubes from the articulated configuration to a non-articulated configuration and the second tube is translatable along the longitudinal axis to move the first and second jaw members from the open configuration to the clamping configuration.

The second tube may be configured to house a cutter shaft therein. The cutter shaft may include a knife assembly having a knife blade configured to reciprocate through knife channels operably disposed on the first and second jaw members upon activation of a trigger assembly associated with the endoscopic forceps. An elongated slot may be defined in at least a portion of the knife assembly and is configured to house a pivot pin and the cam pin therein such that the first and second jaw members are movable independent of the knife assembly.

The endoscopic forceps may be configured to electrosurgically treat tissue and is adapted to connect to a source of electrosurgical energy via a cable.

The second tube may be configured to house a pair of leads of the cable to electrically couple respective seal plates of the first and second jaw members to the source of electrosurgical energy.

A degree of curvature of the bent portion of first tube and a degree of curvature of the bent portion of the second tube may range from about 10 degrees to about 120 degrees.

In certain instance, the endoscopic forceps may include a handle assembly having a movable handle movable relative to a fixed handle. In this instance, the movable handle may be operatively connected to a drive assembly that together mechanically cooperate to impart movement of the second tube.

BRIEF DESCRIPTION OF THE DRAWING

Various embodiments of the present disclosure are described hereinbelow with references to the drawings, wherein.

DETAILED DESCRIPTION

Detailed embodiments of the present disclosure are disclosed herein; however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure Turning now to FIGS. 1A and 1B, an electrosurgical endoscopic forceps 10 (forceps 10) is provided and includes a housing 20, a handle assembly 30, a rotating assembly 80, a trigger assembly 70 and an end effector assembly 100. Forceps 10 further includes a shaft 12 having a first tube 13 with a distal end 14 configured to operably couple to end effector assembly 100 and a proximal end 16 (shown in phantom in FIG. 1A) that extends into housing 20. Forceps 10 also includes cable 310 that connects forceps 10 to a generator 200 or other suitable power source, although forceps 10 may alternatively be configured as a battery powered instrument. Cable 310 includes wires 310a, 310b (see FIG. 2B) extending therethrough that have sufficient length to extend through shaft 12 in order to provide energy to respective jaw members 110 and 120.

Rotating assembly 80 is rotatable in either direction about a longitudinal axis "A-A" that is defined through the shaft 12 to correspondingly rotate end effector 100 about longitudinal axis "A-A." Housing 20 houses the internal working components of forceps 10, such as a drive assembly (not shown), working components of the handle assembly, electrical raceway set-up associated with the cable 310, and other working components therein.

Figure 1A:
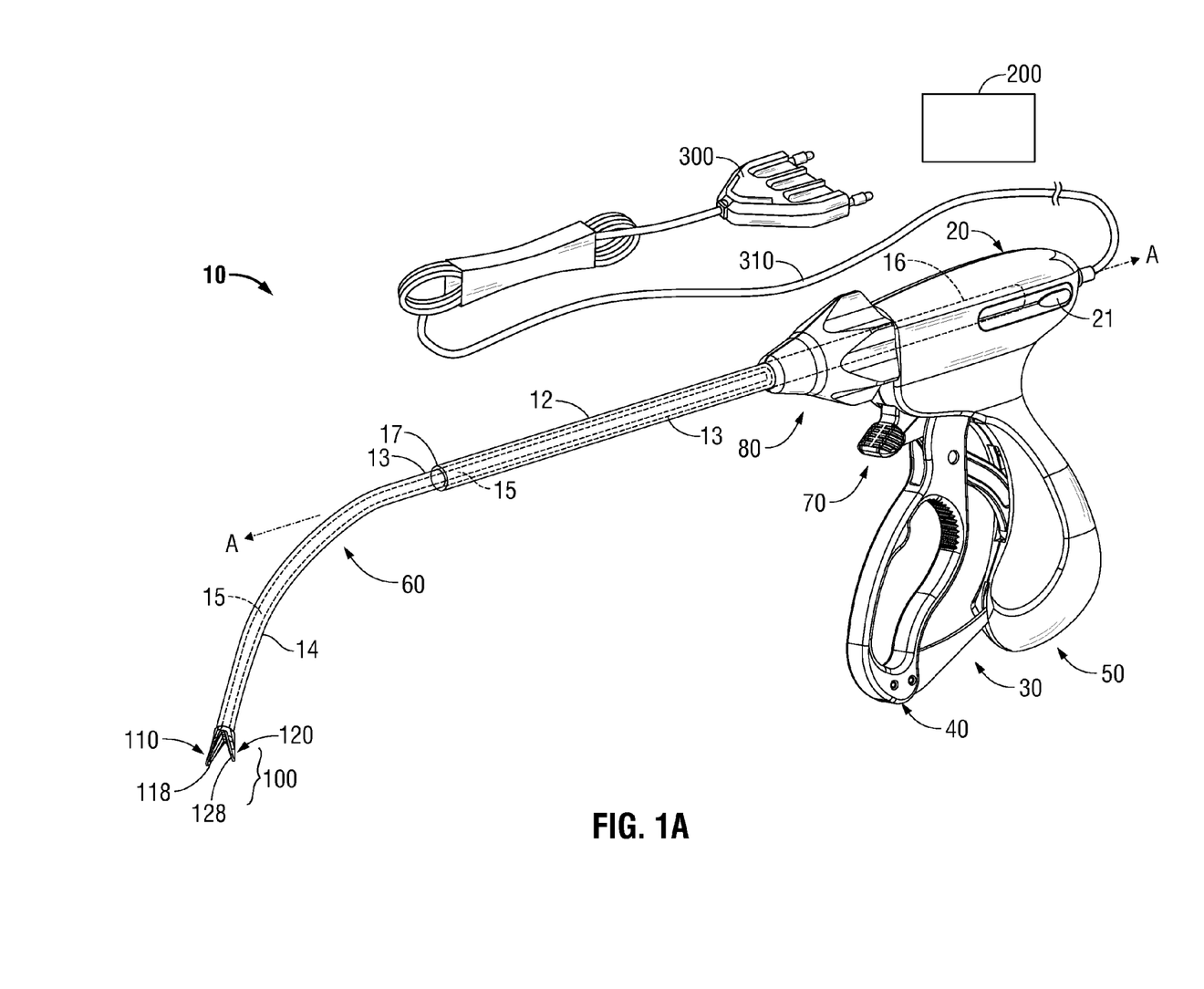
FIG. 1A is a perspective view of an endoscopic bipolar forceps including a shaft with a first tube disposed therein having a bent configuration for positioning an end effector in an articulated configuration according to an embodiment of the present disclosure.
Figure 1B:
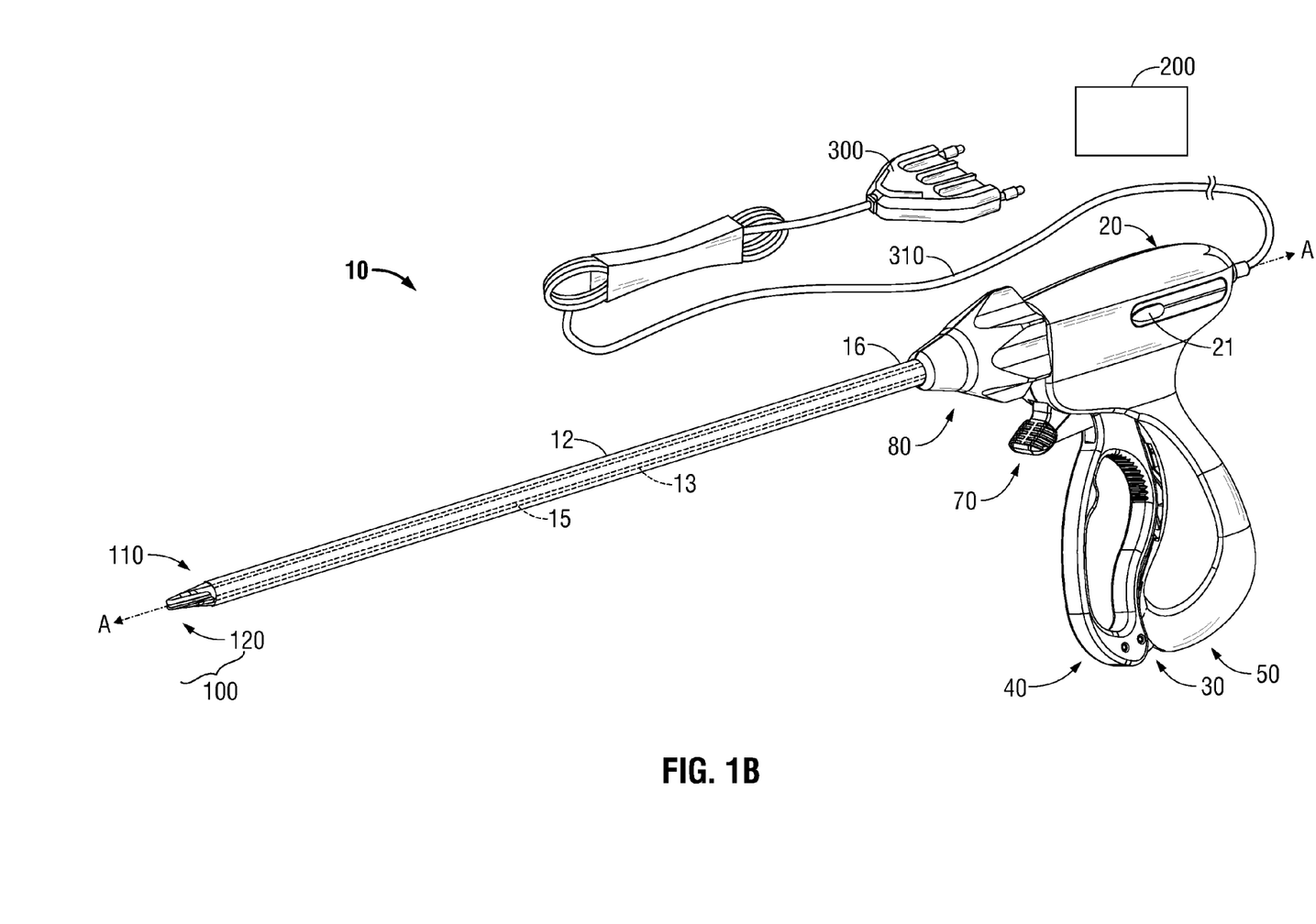
FIG. 1B is a perspective view of an endoscopic bipolar forceps showing the shaft covering the bent configuration and the end effector in a non-articulated configuration.

With continued reference to FIGS. 1A and 1B, handle assembly 30 includes fixed handle 50 and a moveable handle 40. Fixed handle 50 is integrally associated with housing 20 and handle 40 is moveable relative to fixed handle 50. Moveable handle 40 of handle assembly 30 is ultimately connected to a suitable drive assembly that, together, mechanically cooperate to impart movement of jaw members 110 and 120 between a spaced-apart or open position (FIGS. 1A and 2A) and an approximated or clamping position (FIGS. 1B and 2B) to grasp tissue disposed between jaw members 110, 120, respectively. As shown in FIG. 1A, moveable handle 40 is initially spaced-apart from fixed handle 50 and, correspondingly, jaw members 110, 120 are in the spaced-apart position. Moveable handle 40 is depressible from this initial position to a depressed position corresponding to the approximated position of jaw members 110, 120 (see FIG. 1B). Depression of the movable handle 40 imparts distal movement of a second tube 15 that is operably coupled to drive rod (not shown) of the drive assembly, which, in turn, moves the jaw members 110 and 120 from the open configuration to the clamping configuration, described in greater detail below.

Figure 2A:
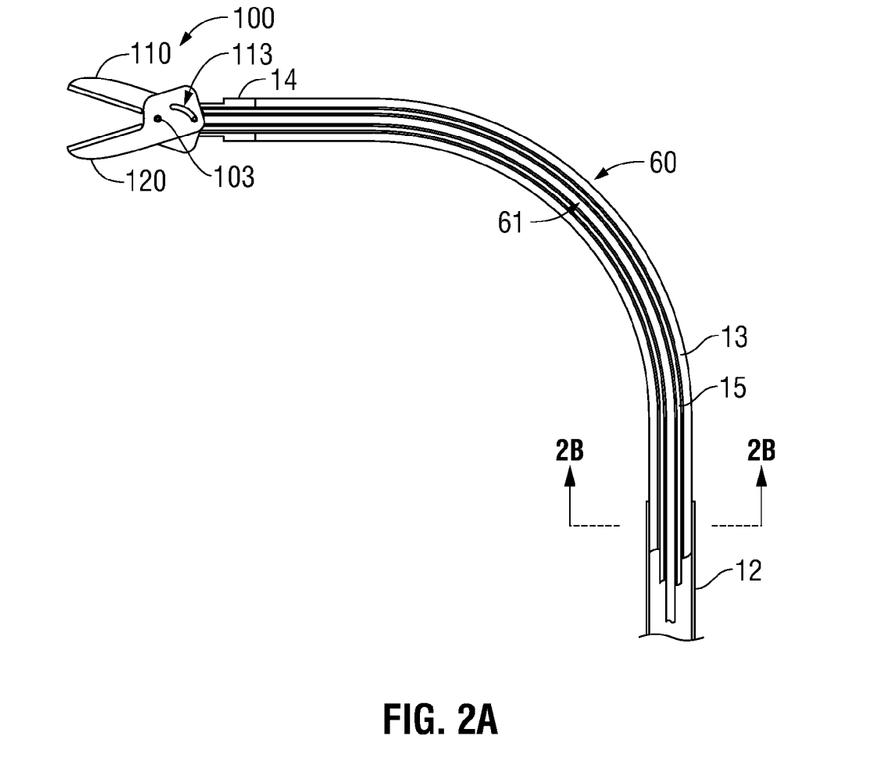
FIG. 2A is a side, cutaway view of a distal end of the endoscopic bipolar forceps depicted in FIG. 1.
Figure 2B:
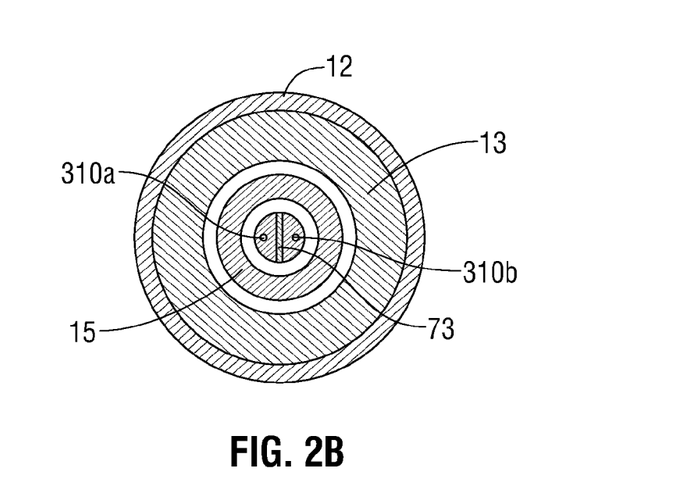
FIG. 2B is a cross-sectional view taken along line-segment 2B-2B in FIG. 2A.

Shaft 12 may be made from any suitable material including, but not limited to surgical steel, plastic, etc. In the embodiment illustrated in FIGS. 1A and 2, shaft 12 is made from surgical steel and includes a generally rigid configuration to move, e.g., "straighten," a bent portion 60 of the first tube 13 to move the jaw members 110 and 120 from an articulated configuration (FIG. 1A) to a non-articulated configuration (FIG. 1B).

Shaft 12 extends a predetermined distance from the housing 20 and defines longitudinal axis "A-A" therethrough (FIGS. 1A and 1B). In particular, shaft 12 extends a predetermined distance from the housing 20 such that in a retracted configuration (e.g., a partially extended configuration) a distal end 17 of the shaft 12 is positioned adjacent the bent portion 60 of the first tube 13 (as best seen in FIG. 1A) and in an extended configuration (e.g., a fully extended configuration) the distal end 17 of the shaft 12 is positioned adjacent the end effector 100 (as best seen in FIG. 1B). Proximal end 16 of the shaft 12 extends within the housing 20 and couples via one or more suitable coupling methods to an actuation mechanism 21 for moving the shaft 12 along the longitudinal axis "A-A." In accordance with the instant disclosure, the distance from the end effector 100 to the distal end 17 of the shaft 12 when the shaft 12 is in the retracted configuration is approximately equal to the distance that the proximal end 16 of the shaft 12 extends into the housing 20. Thus, the proximal most portion of the shaft 12 will be positioned adjacent the distal end of the housing 20 when the shaft 12 is in the extended configuration, see FIG. 1B for example. In certain instances, it may prove advantageous to provide a proximal end 16 of the shaft 12 that is configured for telescopic movement.

Actuation mechanism 21 (FIGS. 1A and 1B), e.g., a button, lever or the like, is operably disposed on the housing 20 to move the shaft 12 along the longitudinal axis "A-A," which, in turn, straightens the bent portion 60 of the first tube 13 (see FIG. 1A and 1B). In the illustrated embodiment, actuation mechanism 21 is in the form of a slide 21 that is operable to effect movement of the shaft 12 along the longitudinal axis "A-A." Slide 21 is movable from a first configuration wherein shaft 12 is in the partially extended configuration adjacent the bent portion 60 (FIG. 1A) to a second configuration wherein shaft 12 is in the fully extended configuration adjacent the end effector 100 (FIG. 1B). Moving the slide 21 from the first configuration to the second configuration allows a user to move the end effector 100 from an articulated configuration (FIG. 1A) to a non-articulated configuration (FIG. 1B).

Figure 3A:
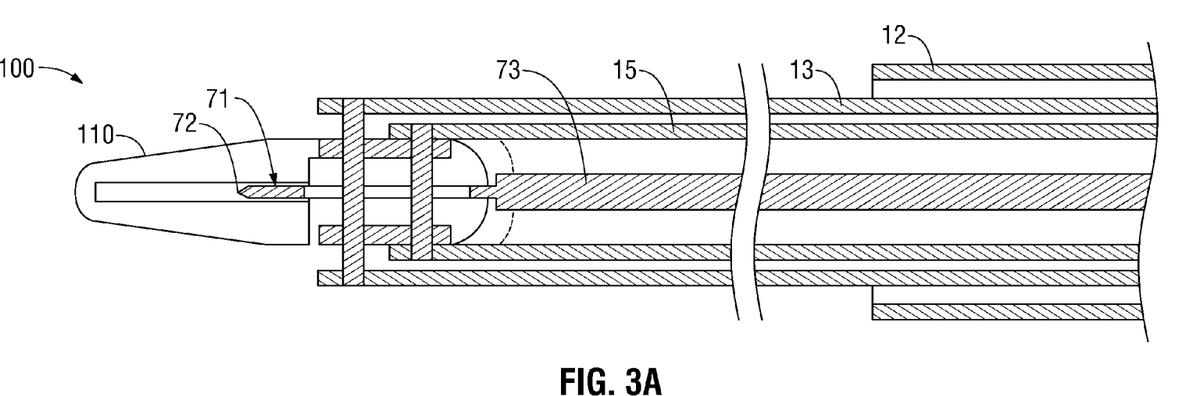
FIGS. 3A and 3B are respective top and side cross-sectional views of the endoscopic bipolar forceps depicted in FIG. 1A.
Figure 3B:
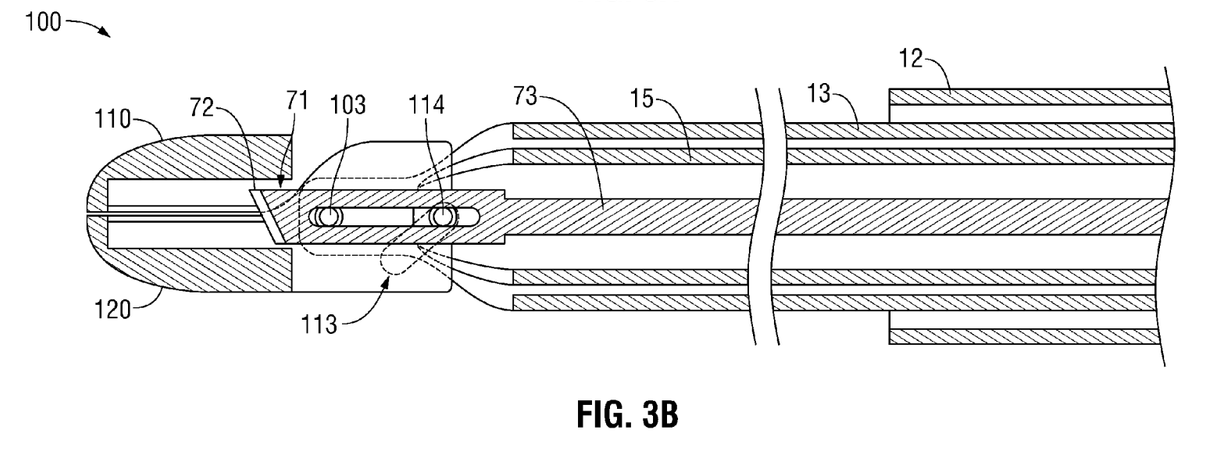

With reference to FIGS. 1A, 3A and 3B, first tube 13 is coaxially disposed within the shaft 12. First tube 13 may be made from any suitable resilient material including, but not limited to, plastic, metal, shape memory alloy, e.g., Nitinol, etc., to provide a suitable combination of stiffness and flexibility; that is, a suitable combination of stiffness and flexibility that allows the bent portion 60 to maintain a normally bent configuration when not under a load, i.e., a load provided by the shaft 12. In the embodiment illustrated in FIGS. 1A, 3A and 3B, first tube 13 is made from a substantially resilient plastic to facilitate moving the first tube 13 from the bent configuration to the "straightened" configuration and vice versa. Bent portion 60 of the first tube 13 includes a degree of curvature that ranges from about 10 degrees to about 120 degrees relative to the longitudinal axis "A-A."

Figure 4:
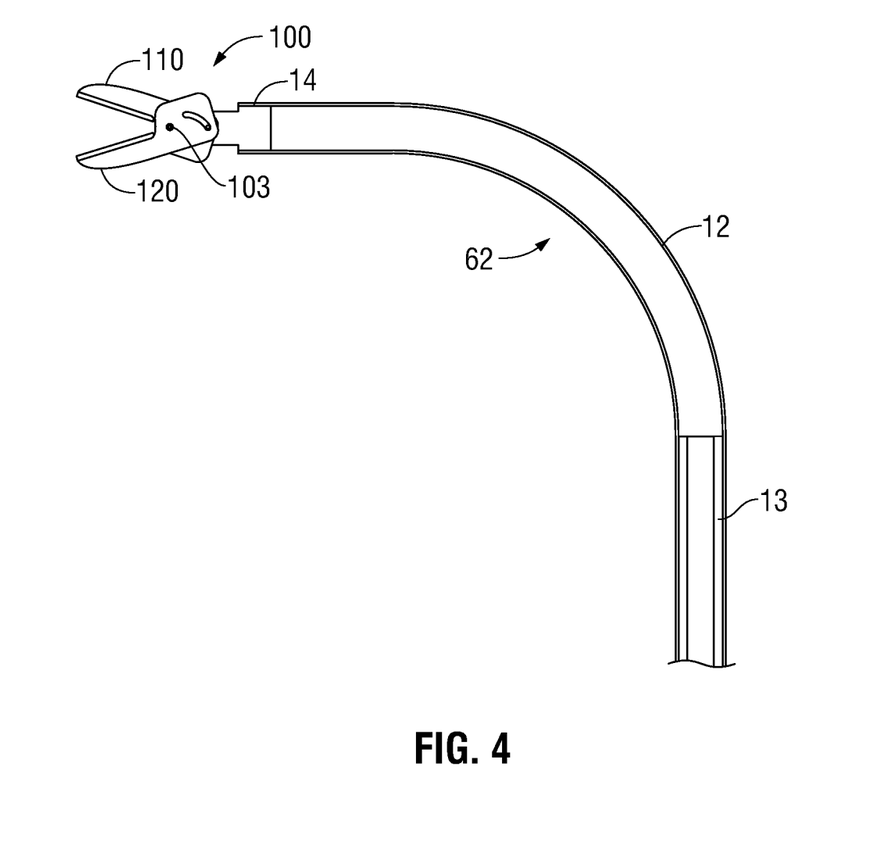
FIG. 4 is a side, cutaway view of the distal end of an endoscopic bipolar forceps according to an embodiment of the present disclosure.

In certain embodiments, the first tube 13 may be configured to function similar to the shaft 12. That is, in this embodiment, the shaft 12 includes a bent portion 62 (FIG. 4) and the first tube 13 is translatable along the longitudinal axis "A-A" to straighten a bent portion 62 of the shaft 12 to move the jaw members 110 and 120 from the articulated configuration to a non-articulated configuration; this embodiment is discussed in greater detail below.

Continuing with reference to FIGS. 2A, 3A and 3B, a second tube 15 is operably disposed within the first tube 13. Second tube 15 includes a bent portion 61 that follows a contour of the bent portion 60 of the first tube 13 (as best seen in FIG. 2A). As with bent portion 60, bent portion 61 is moveable from the bent configuration to a straightened configuration. To this end, second tube 15 may be made from a relatively resilient material similar to first tube 13. As can be appreciated, a degree of curvature of the bent portion 61 is substantially equal to that of the degree of curvature of the bent portion 60 of the first tube 13.

Second tube 15 operably couples to a pair of cam slots 113 (one cam slot is shown in FIG. 2A) via a cam pin 114 on jaw members 110 and 120 to move the jaw members 110 and 120 from the open configuration to the clamping configuration (see FIGS. 1A and 1B). Alternately, or in combination therewith, one or more other types of actuation features such as, for example, linkages, lever arms and the like may be utilized to move the jaw members 110 and 120 from the open configuration to the clamping configuration. Cam pin 114 is positioned through the second tube 15 and housed in an elongated slot 74 on a knife assembly 71 (FIGS. 3A and 3B).

In certain embodiments, second tube 15 is configured to house the pair of leads 310a and 310b of the electrosurgical cable 310 to electrically couple respective seal plates 118 and 128 of the jaw members 110 and 120 to generator 200.

In the illustrated embodiment, second tube 15 is configured to house a cutter shaft 73 therein (FIGS. 3A and 3B). In this instance, knife assembly 71 is operably coupled to the distal end of the cutter shaft 73 and includes a knife blade 72. Knife assembly 71 including knife blade 72 is configured for reciprocation through corresponding knife channels (not shown) on the jaw members 110 and 120. Elongated slot 74 is configured to house the cam pin 114 therein so that the jaw members 110 and 120 may move independent of the knife assembly 71. Elongated slot 74 is also configured to house a pivot pin 103 that extends through the first tube 13 to provide a pivot for the jaw members 110 and 120.

Cutter shaft 73 is translatable within the second tube 15 from a retracted position wherein the knife assembly 71 is positioned at a proximal end of the jaw members 110 and 120 (FIGS. 3A and 3B) to an extended position wherein the knife assembly 71 is positioned at a distal end of the jaw members 110 and 120 (not shown). Movement of the knife assembly 71 from the retracted position to the extended position allows a user to sever tissue clamped between the jaw members 110 and 120, e.g., post electrosurgical treatment of tissue, e.g., tissue that has been sealed.

Referring again to FIGS. 1A and 1B, end effector assembly 100 is shown attached at a distal end 14 of the tube 13 (as best seen in FIG. 3A) and includes opposing jaw members 110 and 120. Each of jaw members 110 and 120 includes an electrically conductive tissue sealing surface 118, 128, respectively. End effector assembly 100 is designed as a bilateral assembly, i.e., where both jaw member 110 and jaw member 120 are moveable about pivot pin 103 relative to one another and to shaft 12, see FIGS. 1A and 1B. However, end effector assembly 100 may alternatively be configured as a unilateral assembly, i.e., jaw member 120 is fixed relative to jaw member 110 which is moveable about pivot 103 and relative to fixed jaw member 120. As noted above, knife assembly 71 is disposed within the second tube 15 and knife channels (not shown) may be defined within one or both jaw members 110, 120 to permit reciprocation of knife blade 72 therethrough, e.g., via activation of trigger 70 of trigger assembly 80.

In use, jaw members 110 and 120 are, initially, in an open configuration and in an articulated configuration as a result of the bent portion 60 of the first tube 13. To move the end effector 100 including the jaw members 110 and 120 from the articulated configuration to a non-articulated configuration, slide 21 is moved distally, which, in turn, moves shaft 12 distally and over bent portion 60 of the first tube 13. As the shaft 12 moves over the bent portion 60, the bent portion 60 and, thus, the end effector 100 including the jaw members 110 and 120 moves toward a non-articulated configuration. The unique configuration of the movable shaft 12 and first tube 15 allows a user to move the end effector 100 including the jaw members 110 and 120 from an articulated configuration to a non-articulated configuration without the use of the aforementioned tendons, links, etc. that are typically associated with conventional forceps, which, as can be appreciated, reduces manufacturing costs of the forceps 10.

To move the jaw members 110 and 120 from the open configuration to the clamping configuration, movable handle 40 is moved through an approximation stroke, i.e., moved proximally toward the fixed handle 50. Movement of the movable handle 40 moves the second tube 15, which, in turn, moves the jaw members 110 and 120 toward one another to clamp tissue therebetween. Subsequently, the clamped tissue may be treated.

In certain instance, it may prove advantageous to sever the sealed tissue. In this instance, trigger assembly 70 may be pressed, which, in turn, advances the cutter shaft 73 including the knife assembly 71 distally and through the knife channels on the jaw members 110 and 120, which, in turn, results in the treated tissue being severed.

From the foregoing and with reference to the various figure drawings, those skilled in the art will appreciate that certain modifications can also be made to the present disclosure without departing from the scope of the same. For example, and as noted above, in embodiments, the shaft 12 may be configured to move from a bent configuration to a straightened configuration to move the end effector 100 including jaw members 110 and 120 from an articulated configuration to a non-articulated configuration. In this instance, shaft 12 includes bent portion 62 (FIG. 4) and is configured to function similar to the first tube 13. As can be appreciated, certain modifications to the forceps 10 may be needed to accommodate this type of configuration. For example, the slide 21 (or other suitable device) may be configured to effect movement of the first tube 13 instead of the shaft 12. Moreover, other types of actuators may be employed to articulate the shaft and position the end effectors relative to tissue, e.g., rotating wheels, knobs, levers, etc.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A forceps, comprising:
   a housing;
   a shaft extending from the housing and defining a longitudinal axis therethrough;
   at least one tube coaxially disposed within the shaft, the at least one tube having a bent portion at a distal end thereof, the bent portion having a contour and defining an articulated configuration in an at-rest condition of the at least one tube; and
   an end effector assembly operatively connected to a distal end of the at least one tube,
   wherein the shaft is translatable along the longitudinal axis to straighten the bent portion of the at least one tube to move the bent portion of the at least one tube from the articulated configuration to a non-articulated configuration, and
   wherein the at least one tube is translatable along the longitudinal axis to actuate the end effector from a first configuration to a second configuration.

2. The forceps according to claim 1, wherein the at least one tube includes a first tube and a second tube, the first and second tubes each having a bent portion at a distal end thereof, the bent portions of the first and second tubes each having a contour.

3. The forceps according to claim 2, wherein the end effector assembly includes first and second jaw members moveable from an first configuration for positioning about tissue to a second configuration for clamping tissue therebetween, the first and second jaw members including respective cam slots defined therein with a cam pin movable therein, the cam pin operably coupling the second tube to the first and second jaw members.

4. The forceps according to claim 3, wherein the second tube is translatable along the longitudinal axis to move the first and second jaw members from the first configuration to the second configuration.

5. The forceps according to claim 4, wherein the second tube is configured to house a cutter shaft therein.

6. The forceps according to claim 5, wherein the cutter shaft includes a knife assembly having a knife blade configured to reciprocate through a knife channel operably defined within at least one of the first and second jaw members upon activation of a trigger assembly associated with the housing.

7. The forceps according to claim 6, wherein an elongated slot is defined in at least a portion of the knife assembly and is configured to house a pivot pin and the cam pin therein such that the first and second jaw members are movable independent of the knife assembly.

8. The forceps according to claim 3, wherein the first and second jaw members are configured to electrosurgically treat tissue and are adapted to connect to a source of electrosurgical energy via a cable.

9. The forceps according to claim 8, wherein the second tube is configured to house a pair of leads of the cable to electrically couple respective seal plates of the first and second jaw members to the source of electrosurgical energy.

10. The forceps according to claim 2, wherein a degree of curvature of the bent portion of the first tube and a degree of curvature of the bent portion of the second tube ranges from about 10 degrees to about 120 degrees.

11. The forceps according to claim 2, further including a handle assembly including a movable handle movable relative to a fixed handle, the movable handle operatively connected to a drive assembly that together mechanically cooperate to impart movement of the second tube.

12. A forceps, comprising:
   a housing;
   a shaft that extends from the housing, the shaft having a bent portion at a distal end thereof, the bent portion having a contour and defining an articulated configuration in an at-rest condition of the shaft;
   first and second tubes coaxially disposed within the shaft and defining a longitudinal axis therethrough; and
   an end effector assembly operatively connected to a distal end of the shaft, the end effector assembly being actuatable by the second tube,
   wherein the first tube is translatable along the longitudinal axis with respect to the shaft to straighten the bent portion of the shaft to move the bent portion of the shaft from the articulated configuration to a non-articulated configuration.

13. The forceps according to claim 12, wherein the end effector assembly includes first and second jaw members, the first and second jaw members moveable from a first configuration for positioning about tissue to a second configuration for clamping tissue therebetween, the first and second jaw members including respective cam slots defined therein with a cam pin movable therein, the cam pin operably coupling the second tube to the first and second jaw members.

14. The forceps according to claim 13, wherein the second tube is translatable along the longitudinal axis to move the first and second jaw members from the first configuration to the second configuration.

15. The forceps according to claim 13, wherein the second tube is configured to house a cutter shaft therein.

16. The forceps according to claim 15, wherein the cutter shaft includes a knife assembly having a knife blade configured to reciprocate through knife channels operably defined within at least one of the first and second jaw members upon activation of a trigger assembly associated with the housing.

17. The forceps according to claim 16, wherein an elongated slot is defined in at least a portion of the knife assembly and is configured to house a pivot pin and the cam pin therein such that the first and second jaw members are movable independent of the knife assembly.

18. The forceps according to claim 13, wherein the first and second jaw members are configured to electrosurgically treat tissue and are adapted to connect to a source of electrosurgical energy via an electrosurgical cable.

19. The forceps according to claim 13, wherein the second tube is configured to house a pair of leads of the electrosurgical cable to electrically couple respective seal plates of the first and second jaw members to the source of electrosurgical energy.

* * * * *